US009782549B2

(12) United States Patent
Riebman et al.

(10) Patent No.: US 9,782,549 B2
(45) Date of Patent: Oct. 10, 2017

(54) DISTANCE INDICATORS FOR MEDICINAL SPRAY DEVICES

(71) Applicant: Ethicon, Inc., Somerville, NJ (US)

(72) Inventors: Jerome Riebman, Basking Ridge, NJ (US); Leo B. Kriksunov, Ithaca, NY (US); Robert J. Tannhauser, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 254 days.

(21) Appl. No.: 14/520,818

(22) Filed: Oct. 22, 2014

(65) Prior Publication Data

US 2016/0114112 A1    Apr. 28, 2016

(51) Int. Cl.
| | |
|---|---|
| *A61M 11/02* | (2006.01) |
| *A61M 11/06* | (2006.01) |
| *A61M 35/00* | (2006.01) |
| *A61B 17/00* | (2006.01) |
| *A61M 11/00* | (2006.01) |

(Continued)

(52) U.S. Cl.
CPC ....... *A61M 11/02* (2013.01); *A61B 17/00491* (2013.01); *A61M 11/007* (2014.02); *A61M 15/0003* (2014.02); *A61B 2017/00495* (2013.01); *A61B 2017/00522* (2013.01); *A61B 2019/461* (2013.01); *A61B 2019/4836* (2013.01); *A61B 2090/0807* (2016.02); *A61M 11/06* (2013.01); *A61M 35/003* (2013.01); *A61M 2202/0225* (2013.01); *A61M 2205/0266* (2013.01); *A61M 2205/13* (2013.01); *A61M 2205/3306* (2013.01)

(58) Field of Classification Search
None
See application file for complete search history.

(56) References Cited

U.S. PATENT DOCUMENTS

| | | | |
|---|---|---|---|
| 4,722,725 | A | 2/1988 | Sawyer et al. |
| 5,849,005 | A | 12/1998 | Garrison et al. |

(Continued)

FOREIGN PATENT DOCUMENTS

WO    WO 01/85355    11/2001

OTHER PUBLICATIONS

International Search Report re: PCT/US15/49295 dated Dec. 11, 2015.
Written Opinion re: PCT/US15/49295 dated Dec. 11, 2015.

*Primary Examiner* — Shaun L David
(74) *Attorney, Agent, or Firm* — David R. Crichton; Leo B. Kriksunov

(57) ABSTRACT

The present invention is directed to a spray applicator for spraying a tissue treatment medicant onto a tissue that has a container containing the medicant and is positioned at a proximal end of the spray applicator; a spray tip positioned at a distal end of the spray applicator; a cannula connecting the container with the spray tip; an actuatable dispensing mechanism at a proximal end of the applicator to express the medicant from the container through the cannula and through the spray tip toward the tissue; an optional pressurized gas source discharging a gas through the cannula in the vicinity of the spray tip or inside the spray tip; and a distance indicator that provides indicia of the distance between the spray tip and the tissue but does not prevent positioning the spray tip closer to the tissue than a defined distance for the distance indicator.

18 Claims, 14 Drawing Sheets

(51) Int. Cl.
*A61M 15/00* (2006.01)
*A61B 19/00* (2006.01)
*A61B 90/00* (2016.01)

(56) References Cited

U.S. PATENT DOCUMENTS

| | | | |
|---|---|---|---|
| 6,004,547 A * | 12/1999 | Rowe | A61B 1/00165 424/426 |
| 6,079,413 A | 6/2000 | Baran | |
| 6,106,497 A | 8/2000 | Wang | |
| 6,461,361 B1 | 10/2002 | Epstein | |
| 6,641,558 B1 | 11/2003 | Aboul-Hosn et al. | |
| 2003/0141376 A1 | 7/2003 | Horan et al. | |
| 2004/0131554 A1 | 7/2004 | Rowe et al. | |
| 2004/0193043 A1 | 9/2004 | Duchon et al. | |
| 2013/0296812 A1 | 11/2013 | Bangera et al. | |

\* cited by examiner

FIG. 11
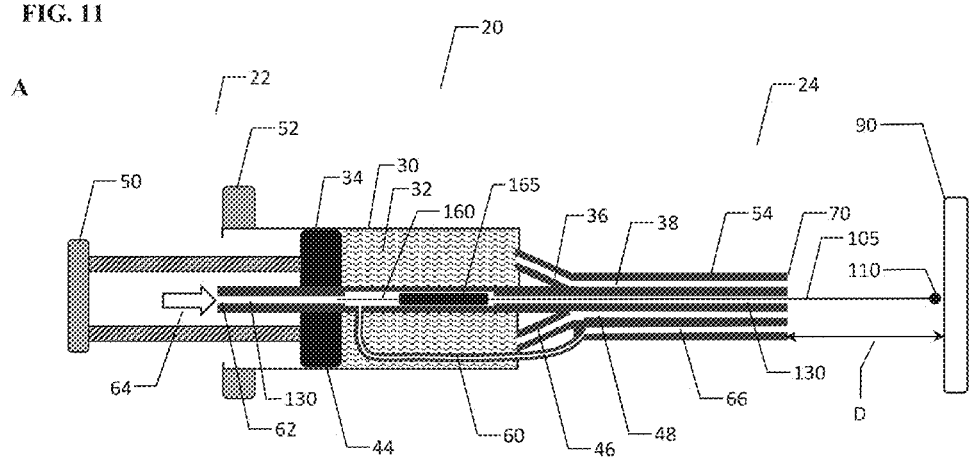
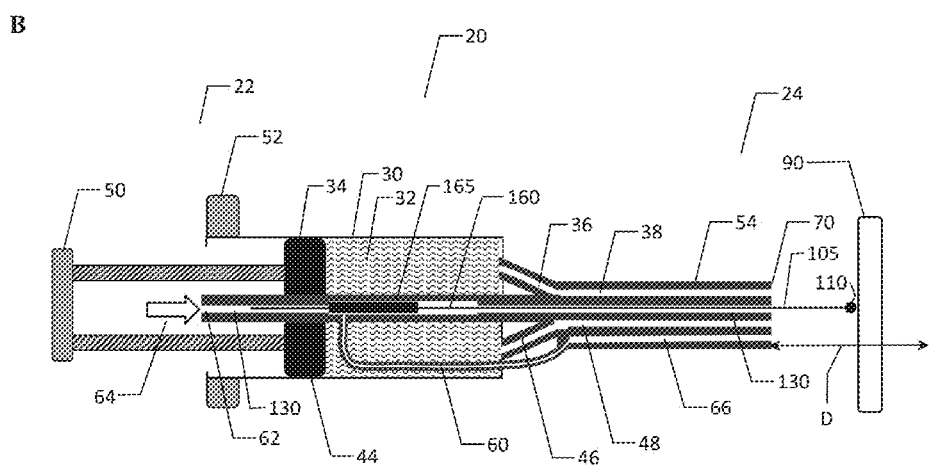

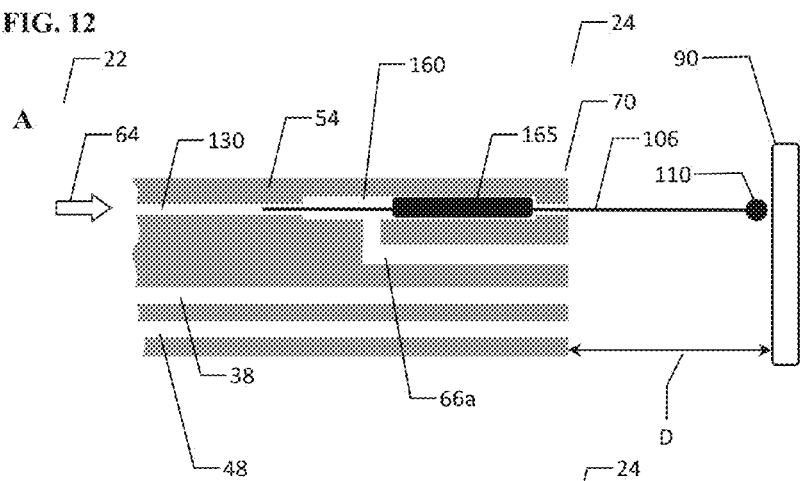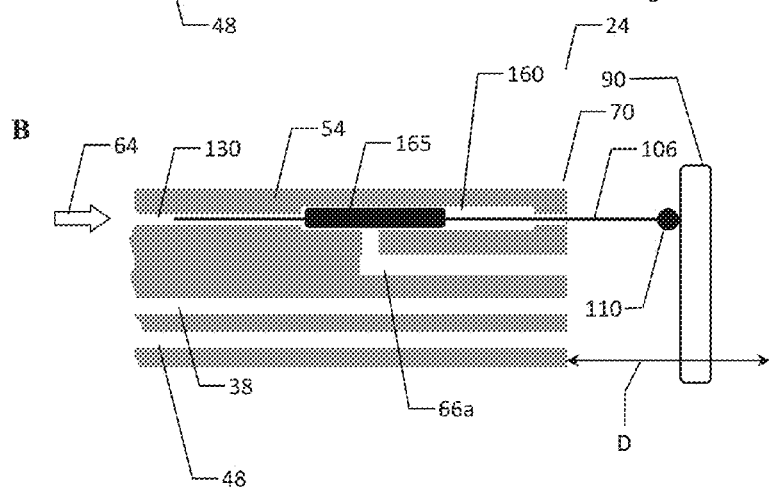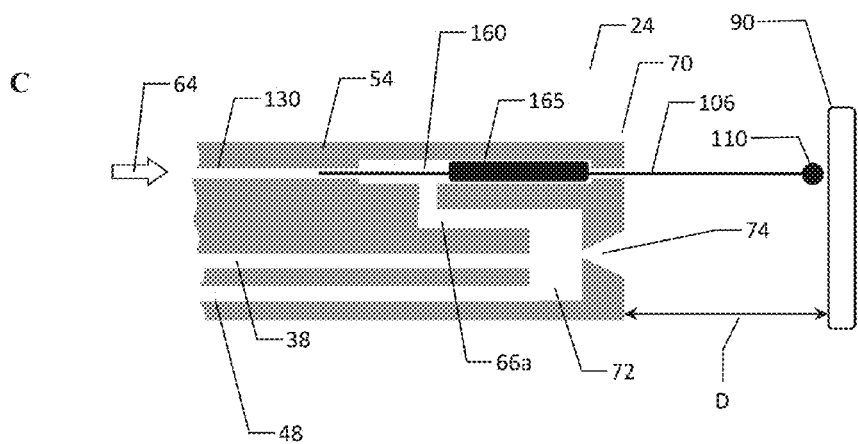
FIG. 12

DISTANCE INDICATORS FOR MEDICINAL SPRAY DEVICES

FIELD OF THE INVENTION

The present invention relates to an applicator and method of applying fluid and powder medicants to biological tissue for wound sealing, hemostasis, and therapeutic treatments, and is particularly useful for applying medicants with gas-assisted spray from a hand-held applicator. The invention further relates to distance indicators for estimating the distance from the spray tip to the surface of tissue and ensuring that the spray is preformed not closer than the minimum recommended spray distance.

BACKGROUND OF THE INVENTION

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. The control of bleeding is essential and critical in surgical procedures to minimize blood loss, to reduce post-surgical complications, and to shorten the duration of the surgery in the operating room.

Known hemostatic and sealant materials include absorbable liquid sealants such as fibrin sealants which are formed from blood plasma components and comprise a first agent containing fibrinogen and a second agent which usually includes thrombin. Fibrinogen is capable of a polymerizing to form a solid fibrin clot when the agents are mixed. Other hemostatic materials for controlling excessive bleeding include Topical Absorbable Hemostats (TAHs) which are widely used in surgical applications. TAHs encompass products based on oxidized cellulose (OC), oxidized regenerated cellulose (ORC), gelatin, collagen, chitin, chitosan, etc. These materials can be delivered in solid form, as scaffolds, as suspensions or paste, or as powders.

Application of any medicants, including biological sealants, to target areas, requires accurate mixing and targeting, particularly when a multi-part sealant is used, due to the rapid polymerization upon interaction of the components. For delivery of fibrin sealant, for example, the two components are typically dispensed simultaneously from separate devices, such as syringes, and mixed together immediately prior to application or on the tissue surface.

Gas-assisted application of sealant, such as through use of a syringe described above, is frequently used to deliver the sealant to the desired site, and sometimes pressurized and atomized application of the sealant is useful. For spraying fluids, such a multi-part sealant, as well as for spraying powders, mixing, accuracy, and efficiency of the spraying is frequently helped by use of compressed gas. Gas-assisted spray uses gas pressure to spray the material directly at the intended site, helping targeted delivery, atomization, and ease of application. A pressurized, typically sterile gas, such as air, nitrogen, carbon dioxide, and the like, atomizes and propels the sprayed material towards the surface of the tissue.

Maintaining optimal distances from the dispensing nozzle to the treated areas of tissue during dispensing of the tissue sealants and hemostats is important for optimal mixing of the components, optimal spray patterns, and, especially but not only in cases of gas-assisted delivery, for avoiding gas embolisms. Maintaining optimal distances is especially important during laparoscopic delivery due to difficulties in reliably estimating distances in a laparoscopic environment.

U.S. Pat. No. 6,461,361 "Gas-driven spraying of mixed sealant agents", discloses that a gas-driven spray applicator suitable for spray delivery of mixed fibrin sealants for surgical use has a spray nozzle wherein droplets or a stream of mixed sealant agents are entrained in a stream of gas such as sterile compressed air. Gas entrainment of the mixed sealant overcomes problems of ineffective mixing which may occur when the sealant agents are separately discharged into overlapping spray patterns. A spray tip assembly is disclosed which is suitable for attachment to an applicator body having manually dischargeable reservoirs for the sealant agents.

U.S. Pat. No. 6,461,361 further discloses a spray applicator for spraying a liquid sealant comprising at least two sealant agents capable of coagulating when mixed together, the applicator comprising: a) a spray hood defining a spray volume; b) a sealant delivery pathway extending from individual sources of the respective sealant agents to the spray volume for delivery of the at least two sealant agents to the spray volume; c) a pressurized gas inlet to generate a gas stream into the spray volume, wherein the sealant delivery pathway can deliver the at least two sealant agents to the gas stream to generate a spray containing the at least two sealant agents, wherein the pressurized gas inlet is connectable to a source of pressurized gas being a compressed air supply, a surgical operating room gas supply or a portable container of compressed gas; and d) a spacer element extending in the direction of spraying to maintain a desired distance between the spray volume and a work surface.

U.S. Pat. No. 6,461,361 further discloses a spray tip assembly intended to be attached to a spray applicator body to provide a spray applicator for spraying a liquid sealant comprising at least two sealant agents capable of coagulating when mixed, the applicator body having: a) at least two reservoirs respectively for storing the at least two sealant agents; b) at least two conduits for separately dispensing the at least two sealant agents; and c) a manually actuatable dispensing mechanism to discharge the sealant agents from the reservoirs through the at least two conduits; d) at least two sealant agent receiving ports connectable with the at least two conduits; e) a mixing chamber to receive and mix the at least two sealant agents from the at least two sealant receiving ports to provide mixed sealant; f) a spray hood defining a spray volume; g) a delivery conduit to receive mixed sealant from the mixing volume and deliver the mixed sealant to the spray volume; h) a pressurized gas inlet to generate a gas stream into the spray volume; wherein the delivery conduit extends into the path of the gas stream to deliver the mixed sealant to the gas stream, to generate a spray of mixed sealant droplets; and i) a spacer element extending in the direction of spraying to maintain a desired distance between the spray volume and a work surface. The assembly described is bulky, not laparoscopically deployable, can interfere with the spray, and prevents the spray performed closer to the surface when no gas assist is used.

U.S. Pat. No. 6,641,558 "Method and apparatus for preventing air embolisms" discloses method and apparatus for preventing air embolisms during surgical procedures which involves providing a fluid source in communication with an aperture extending into an anatomical cavity such that fluid may be delivered into the cavity when a condition of negative pressure exists in the cavity, thereby preventing the introduction of air into the cavity.

U.S. Pat. No. 4,722,725 "Methods for preventing the introduction of air or fluid into the body of a patient" discloses a method for preventing the introduction of ambient air into the vascular system of a patient through catheter means introduced into said vascular system during intravenous or intra-arterial procedures which comprises: providing the catheter means with fluid flow control means comprising: a tubular structure including input means and output means; each provided with an open bore constituting a flow channel; and further means located between the bores of said input and output means of said tubular structure and having an open and a closed position, said further means providing for a connecting channel between said bores when said further means is in the open position, said further means normally being prestressed to said closed position and being forcible to said open position in response to a positive fluid pressure in the bore of either of said input or output means, said further means being constructed and arranged so as to return to said closed position in response to a removal of positive fluid pressure from said bore containing same; introducing the catheter into the vascular system of the patient during intravenous or intra-arterial procedures; and introducing a fluid into said patient through said fluid flow control means and catheter means by directing the fluid under a positive pressure above that of ambient air into the bore of the input means of said fluid flow control means so that the fluid flow control means remains competent in response to ambient air pressure in the bore of said input means but which opens in response to said positive fluid pressure to allow flow therethrough, while also preventing the introduction of air into the vascular system of the patient.

U.S. Pat. No. 6,106,497 "System and method for preventing an air embolism in a surgical procedure" discloses a system for preventing an air embolism in the brain of an animal in a cardiovascular surgical procedure, comprising: a) a source of a gas; b) a mechanism for controlling pressure and flow of the gas therethrough, having an inlet end and an outlet end, the inlet end being connected to the gas source; and c) a tube for conveying the gas therethrough having a first end and a second end, and a member for preventing blood from flowing from the heart into the gas conveying tube; the first end adapted for placement in the heart of the animal and having a plurality of apertures for passage of the gas therethrough into the heart; wherein the pressure/flow controlling mechanism is disposed between the gas source and the gas conveying tube; and the gas source, the pressure/flow controlling mechanism and the gas conveying tube are in fluid flowing communication for conveying the gas therethrough; and the pressure/flow controlling mechanism is operable to provide a flow of the gas through the system such that when the first end of the gas conveying tube is placed into the heart, the pressure and flow of the gas from the pressure/flow controlling mechanism through the gas conveying tube into the heart is effective to inhibit air from entering the heart, great vessel, or both, or to remove air from the heart, the great vessel, or both.

U.S. Pat. No. 5,849,005 "Method and apparatus for minimizing the risk of air embolism when performing a procedure in a patient's thoracic cavity" discloses a method of minimizing the risk of air emboli in a patient's circulatory system when performing a procedure in the patient's thoracic cavity, comprising the steps of: inserting an instrument delivery member into a patient's thoracic caviler thereby forming a first percutaneous penetration, the instrument delivery member having a through hole sized to permit an instrument to pass therethrough; coupling an outlet from a source of gas to the instrument delivery member; injecting the gas from the source of gas into the patient's thoracic cavity through the outlet coupled to the instrument delivery member, the injecting step being carried out with a plurality of outlets coupled to the instrument delivery member for passing the gas into the patient's thoracic cavity, the injecting step being carried out so that the gas issuing from the plurality of outlets forms a gas shield across the through hole.

There is an unmet need in sealant or hemostat dispensing devices that are ensuring that spray is preformed not closer than the minimum recommended spray distance.

SUMMARY OF THE INVENTION

In one aspect, a spray applicator for delivery of a medicant onto a tissue surface comprises a container containing a medicant and positioned at a proximal end of the spray applicator; a spray tip positioned at a distal end of the spray applicator; a cannula connecting the container with the spray tip; a dispensing mechanism at a proximal end of the applicator to express the medicant from the container through the cannula and the spray tip toward the tissue surface; a distance indicator that is deployable between the spray tip and the tissue and provides visual or tactile observation indicia of distance but does not prevent positioning of the spray tip closer to the tissue than the observed distance; and an optional pressurized gas source in fluid communication with the spray tip through the cannula providing gas in the vicinity of the spray tip or within the spray tip. The indicator can be a fixed length of a flexible metal wire that is slidably installed in the cannula with a proximal end of the wire observable at the proximal end of the spray applicator with a distal end of the wire extending from the spray tip, with the position of the wire relative to the tissue surface detectable at the proximal end of the spray applicator. In another aspect, the distance indicator is deployable from the cannula and optionally retrievable into the cannula, with a distal portion of distance indicator extending directionally towards the tissue and having length equal to a minimum recommended spray distance. In another aspect, the proximal portion of distance indicator can be tactilely felt for detecting proximity of the spray tip to the tissue surface. In another aspect, the distance indicator moderates or fully blocks gas delivery to the spray tip when the distance indicator touches the tissue surface.

In yet another aspect, a method for spraying the medicant onto the tissue surface comprises operating the spray applicator to deploy the distance indicator towards the tissue surface, observing the distance indicator and, if necessary, adjusting the distance between the spray tip and the tissue surface relative to a generally recognized or clinically relevant recommended spray distance, and then expressing medicant onto the tissue surface via a gas-assisted spray.

BRIEF DESCRIPTION OF THE FIGURES

FIG. 1 shows a schematic cross-sectional view of an embodiment of a spray applicator device of the present invention.

FIG. 2 shows a schematic cross-sectional view of an embodiment of a spray applicator device of the present invention.

FIG. 3 shows a schematic cross-sectional view of an embodiment of a spray applicator device of the present invention.

FIG. 11 shows a schematic cross-sectional view of embodiments of a spray applicator device of the present invention.

FIG. 12 shows a schematic cross-sectional view of embodiments of the cannula and the cannula tip of the present invention.

Figure 17:
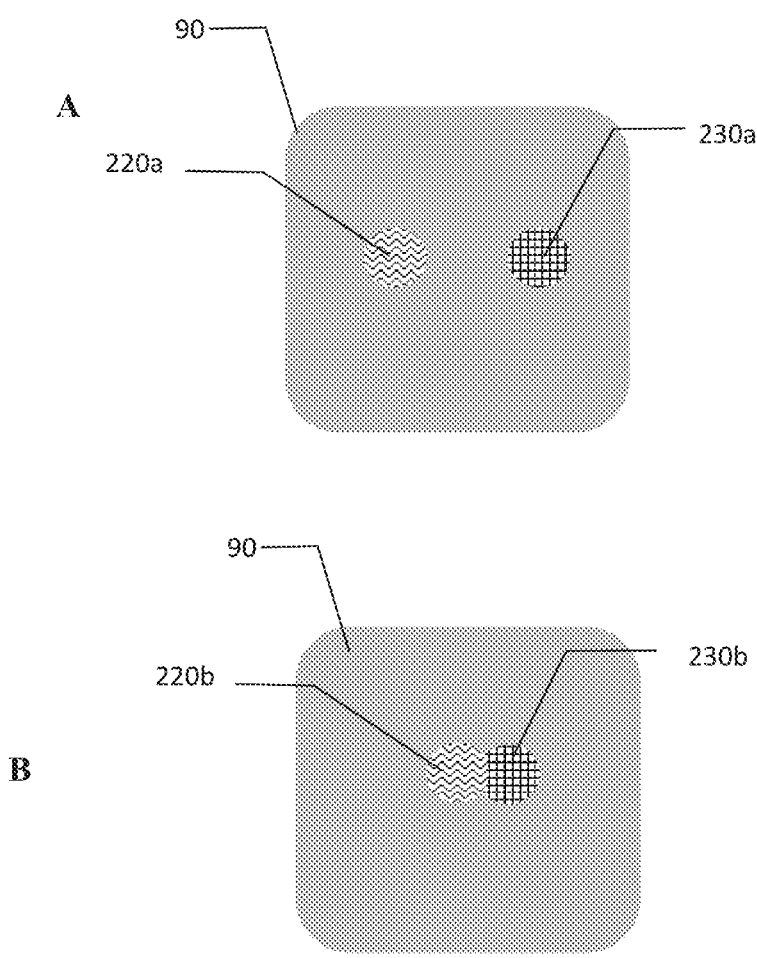

FIG. 17 schematically shows mutual positioning of light beams spots on tissue as generated by an embodiment of a spray applicator device of the present invention.

DETAILED DESCRIPTION OF THE INVENTION

Some of the objectives of the present invention is to provide for medicant dispensing devices that: 1) are capable of calibration or provide distance indicators that estimate the distance from the spray nozzle or spray tip to the surface of tissue and ensuring that spray is performed not closer than the minimum recommended spray distance; 2) provide that the indicators do not interfere with the spray and can be removed or are not interfering when no gas assist spray is used and the spray can be performed closer to the surface when no gas assist is used; 3) provide that the indicators can be deployed and removed manually or automatically; 4) optionally provide that the indicators control the gas pressure automatically; 5) optionally provide that the indicators are deployable laparoscopically, i.e. can be inserted through a trocar; 6) in cases of powder delivery (powdered fibrinogen, powdered thrombin, ORC powder, and the like powders and mixtures thereof), provide that the distances from tissue are known and/or controlled to avoid material embolism (entraining of a material in a blood vessel) or in case of gas-assisted delivery, gas embolism; and 7) in cases of non-gas assisted delivery, as the hydraulic pressure or such other force of the spray stream can also be related to a material embolism, providing that the distances from tissue are known and/or controlled for avoiding embolisms.

Some surgery practitioners may find it difficult to correctly estimate the actual distance between a spray tip and the nearest treated tissue surface, especially in laparoscopic environment. According to one aspect of the present invention, an indicator of the minimum recommended distance between the spray tip and the tissue and of actual spraying distance is positioned between the spraying/dispensing end of the tissue treatment medicant delivery device and the surface of the tissue that is being treated. The indicator helps to reduce the risk of embolism, such as gas embolism, or any material embolism, as it enables the user to deliver the medicant by spray in accordance with the recommended operational guidelines by maintaining the minimum recommended distances from the tissue surface. The indicator further helps to spray from an optimized distance, so that a necessary overlap of the spray patterns is achieved.

The indicator is not a spacer in the sense that it provides an estimate to the health practitioner of the distance between the spay tip and the tissue surface, but it does not prevent spraying in closer proximity to the surface, i.e. closer than the general minimum recommended distance indicated by the indicator, which may be appropriate when a) specific tissue being treated has low susceptibility to embolisms; b) gas pressure is reduced or turned off, such as with the air-less or gas-less spray; c) when spraying over a solidified coating or an implant which makes formation of an embolism highly unlikely; or d) when it is needed based on clinical judgment or the surgical procedure.

Advantageously, the distance indicators of the present invention are laparoscopically deployable and compact, and can be deployed when needed only or to be retrieved after deployment so as to not to interfere with the spray. The distance indicators ensure that gas-assisted spray can be performed not closer than the generally recommended minimum spray distance, unless a clinical decision is made to spray from a closer distance, such as in a case of gas-less spray.

An embolism is defined for purposes of this disclosure broadly as the condition whereby spraying fluid or solid material (such as powder), or mixtures thereof, onto tissue surface results in entrainment of the material into the blood stream with the potential for blockage of the blood vessels. The blockage can occur with the material being sprayed such as gas, fluid or powder, or with the resulting clots. The embolism is further defined as obstruction of an artery, typically by a clot of blood, a bubble formed by any gas such as air, or by particulate material.

In one aspect, with no gas assist being used, the distance indicators of the present invention are used to define distance to the tissue for preventing material embolism, i.e. fluid or powder entrainment into the blood stream. In case of powder delivery (fibrinogen powder, thrombin powder, ORC powder, gelatin powder, and the like, and combinations thereof), the generally recommended minimum distances from tissue are in many instances clinically believed to avoid material embolism (entraining of a material in a blood vessel), similar to the situations of gas-assisted delivery, to avoid gas embolism. Gas embolisms, material embolisms, and combinations of gas embolisms and material embolisms can be made less probable or prevented by utilizing distance indicators of the present invention.

Figure 1:
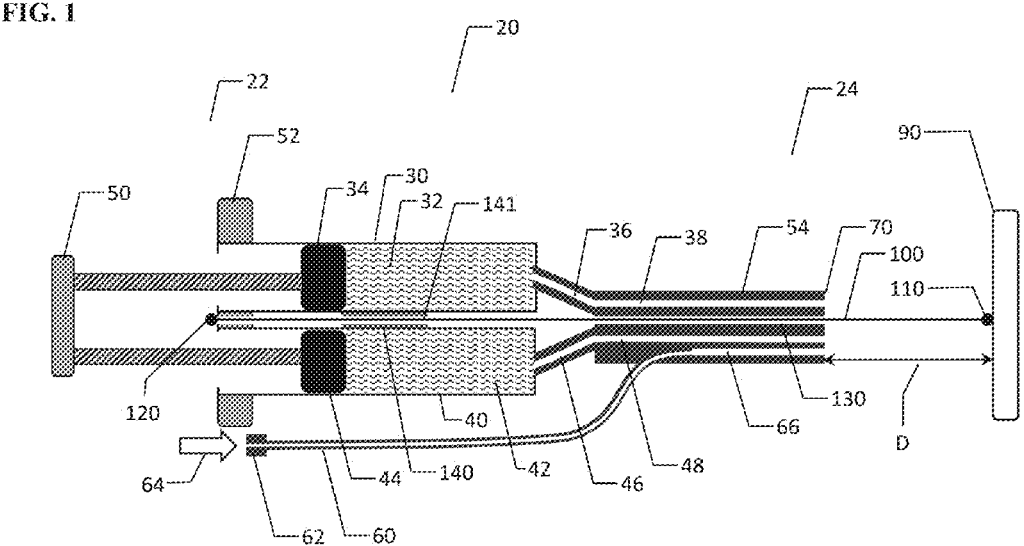

Referring to FIG. 1, a schematic cross-sectional view of spray applicator device 20 suitable for delivery of a tissue treatment medicant onto tissue 90 is presented. Device 20 has a proximal end 22 for gripping which is typically positioned distally from tissue 90, and a distal end 24 that is positioned proximally to tissue 90. Device 20 comprises container containing the medicant, such as a dual barrel syringe with first barrel 30 containing a first component 32 (such as fibrinogen) of two-part sealant and second barrel 40 containing a second component 42 (such as thrombin) of two-part sealant. Container containing the medicant can be integral with spray applicator device 20, as shown in FIG. 1, or alternatively it can be connected to spray applicator device 20 via an elongated conduit (not shown) conveying the medicant towards distal end 24 for expression on tissue 90. First barrel 30 and second barrel 40 have respectively first plunger 34 and second plunger 44 for expressing first component 32 and second component 42 via exit ports 36 and 46. The expression of first component 32 and second component 42 is effected by action of an actuatable dispensing mechanism (which can be actuated, for instance, manually), such as handle 50 which is depressed to move plungers 34 and 44 towards distal end 24 of device 20 within barrels 30 and 40. Handle 50 is most conveniently depressed by pushing while holding handgrip 52. Exit ports 36 and 46 are connected to flexible elongated delivery cannula 54, with first component 32 passing via conduit 38 and second component 42 passing via conduit 48 to spray out of cannula tip or spray tip 70 at the distal end 24. Spraying towards tissue 90 is performed from a generally recommended minimum distance D indicated by arrow D or preferably from distance equal to or larger than D. In some situations, spraying can be performed from a distance that is less than the minimum recommended distance D, such as when no gas assist is used.

Minimum recommended spray distance D can be different depending on the type of gas assist, gas pressure used, tissue type, and materials delivered, with the clinically recommended distance varying from about 1 cm to about 20 cm, such as 4 cm, 5 cm, 6 cm, 8 cm, 10 cm, or 15 cm.

Gas assisted spray, with the gas being any clinically acceptable gas, such as either air, nitrogen, argon, carbon dioxide or a mixture thereof, is performed via connecting a compressed gas source to port 62, with gas flow direction schematically shown by arrow 64. Gas flows through gas supply line 60 connected to delivery cannula 54, flowing via gas conduit 66 to exit delivery cannula 54 out of the tip 70 towards tissue 90.

Distance indicator 100 comprises a retractable flexible wire or rod, such as one made of a polymer, such as polyethylene, e.g. high density polyethylene (HDPE), or of a flexible alloy, e.g. Nitinol or stainless steel. Distance indicator 100 is positioned within delivery cannula 54 by being slidably disposed in an indicator conduit 130. The diameter of the indicator 100 is from about 0.2 mm to about 2 mm, more preferably from 0.25 mm to about 1 mm, such as 0.3 mm, 0.5 mm, or 0.75 mm. Distance indicator 100 has at the distal end an indicator tip 110 which optionally comprises an enlarged indicator tip 110 which has larger dimensions relative to the diameter of the indicator 100. In some embodiments (as shown in FIG. 1) indicator tip 110 optionally comprises a ball having a diameter that is larger than the diameter of indicator 100, such as 2, 3, 4, 5, or 10 times larger, preventing injury to tissue 90 by tip 110. In some embodiments (not shown) indicator tip 110 optionally comprises a bend in the wire comprising distance indicator 100.

Distance indicator 100 passes through an optional alignment member 140 with alignment conduit 141 that is positioned on first barrel 30 or on second barrel 40 or alternatively between first barrel 30 and second barrel 40 and terminates in a proximal tip 120, situated in proximity to handgrip 52. Proximal tip 120, in some embodiments (as shown in FIG. 1), optionally comprises a ball having a diameter which is larger than the diameter of the indicator 100, such as 2, 3, 4, 5, or 10 times larger.

Device 20 has delivery cannula 54 which is preferably laparoscopically deployable and has outer diameter less than the trocar clearance, such as 3 mm, 4 mm, 5 mm, 8 mm, or 10 mm, preferably not more than 5 mm.

In operation, a device operator or assistant optionally inserts the delivery cannula 54 through a trocar (if a procedure is being performed laparoscopically) and directs the cannula tip 70 towards tissue 90. The operator then deploys the indicator 100 by advancing indicator tip 110 distally towards tissue 90 by pushing on proximal tip 120. The distance from the tissue 90 can, in one embodiment, be determined or at least estimated visually (with the optional use of cameras and or endoscopes) by observing that indicator tip 110 is not touching the tissue when the indicator 100 is fully extended from delivery cannula 54 tip 70 as shown in FIG. 1, with length of exposed indicator 100 substantially equal to D. The visual determination then establishes that the distance between cannula tip 70 and tissue 90 is substantially equal to or larger than minimum recommended distance D.

In another embodiment, the distance can be determined or estimated visually by observing the position of the proximal tip 120, which when it is in the most distally advanced position, i.e. most advanced position towards tissue 90, as shown in FIG. 1, indicates that distance between cannula tip 70 and tissue 90 is substantially equal to or larger than minimum recommended distance D.

In other embodiments, the distance can be determined or estimated by tactilely feeling the resistance from the contact of the indicator tip 110 against tissue 90 at the proximal tip 120 or by tactilely feeling the position of the proximal tip 120 and detecting whether it is in the most advanced towards tissue 90 position (as shown in FIG. 1).

Figure 2:
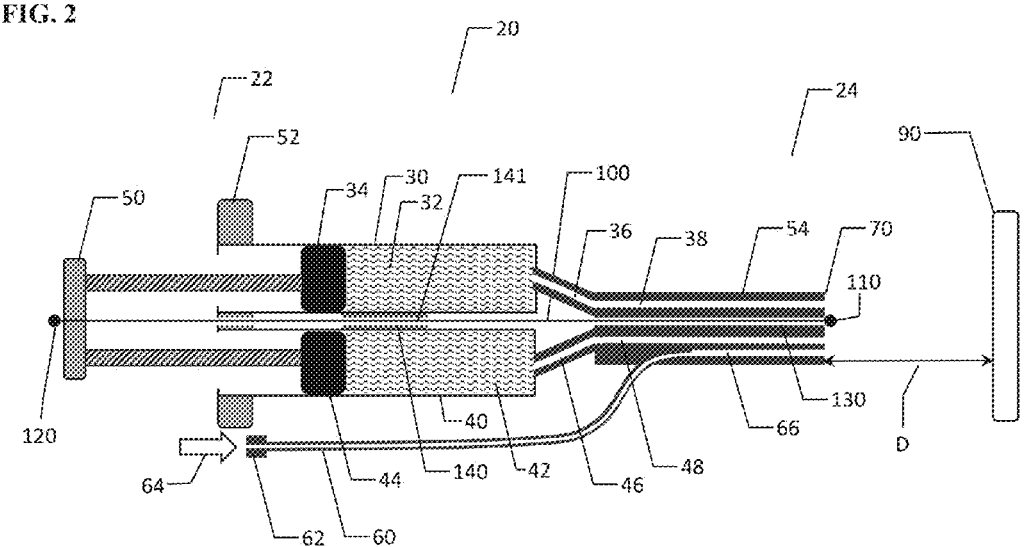

The device operator can adjust the distance as needed based on any of the above observation points or combinations thereof. After determining that the distance from cannula tip 70 to tissue 90 is substantially equal to or larger than the minimum recommended distance D, the operator can optionally retract the indicator 100 by pulling on proximal tip 120 to retrieve the indicator 100 proximally and consequently decrease any potential interference with the spray, as shown in FIG. 2. The practitioner then initiates delivery of medicant by expressing first component 32 and second component 42 by action of handle 50 moving plungers 34 and 44 towards distal end of device 20 and optionally simultaneously activating gas delivery from compressed gas source connected to port 62, resulting in gas-assisted spray from cannula tip 70. Thus, when performed in this manner, the delivery of a gas-assisted spray is performed at a distance that is equal or larger than the minimum recommended distance D.

Indicator 100 can be re-deployed as needed for subsequent estimates of distance between tissue 90 and cannula tip 70. In case of gas-less spray, indicator 100 can be kept non-deployed, i.e. kept in the retrieved position that is pulled proximally and furthest from tissue 90, as shown in FIG. 2. Optionally, if the gas assisted spray is not being used, distance indicator 100 can be completely removed from device 20.

In one embodiment, indicator 100 can also have optional distance indicating markings at the distal end (not shown in FIGS. 1-2), which are then observable by an operator or assistant during the procedure. In another embodiment, indicator 100 can also have optional distance indicating markings at the proximal end (not shown in FIGS. 1-2) that are then observable by the user or assistant during the procedure. Optionally, the length of the exposed indicator 100 at the distal end is settable from the proximal end and can be selected according to specific procedure or specific gas pressure to be used.

Figure 3:
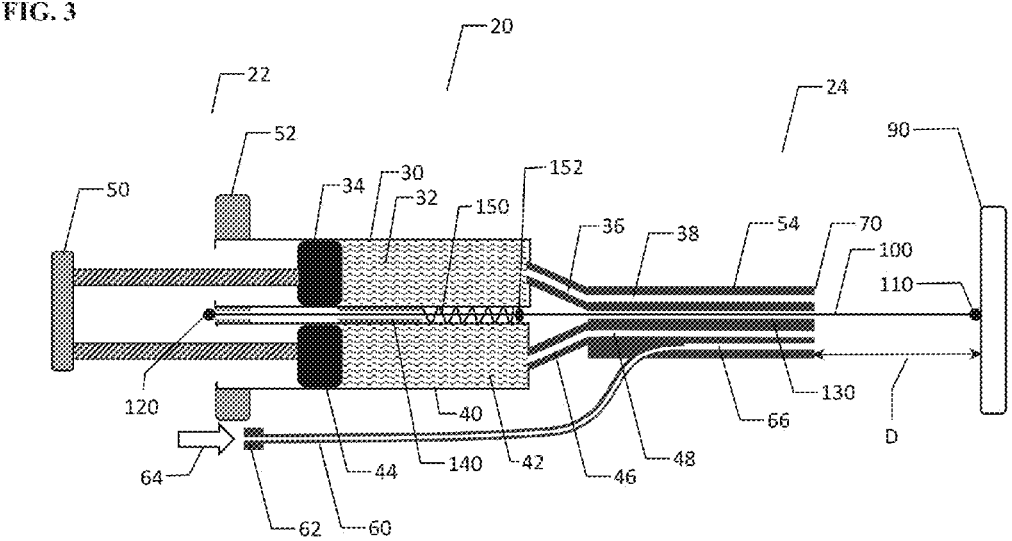

Referring to FIG. 3, in one embodiment, an optional spring 150 is positioned on distance indicator 100 between the alignment member 140 positioned proximally and a spring retainer 152 positioned distally. Spring 150 provides for a resilient positioning of the distance indicator 100 against tissue 90, i.e. in a distally advanced position, whereby when the tip 110 is pushed against the tissue, distance indicator 100 resiliently retreats proximally, compressing the spring 150 and providing an indication to the operator or practitioner that the distance is less than the minimum recommended distance D. Prior to spray, if needed, the practitioner can optionally retract the indicator 100 by pulling on proximal tip 120 retrieving the indicator 100 proximally, compressing the spring 150, to decrease any potential interference with the spray.

Figure 4:
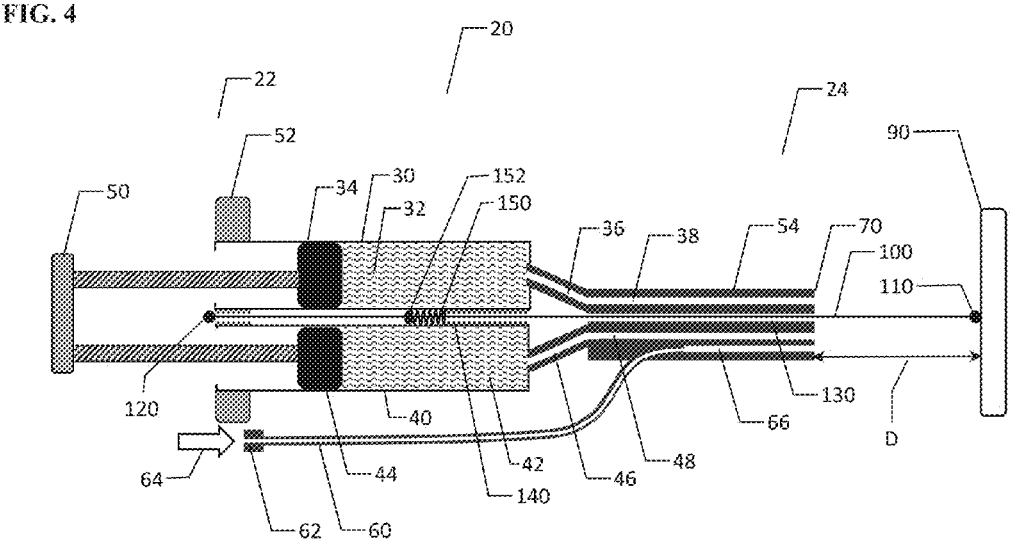
FIG. 4 shows a schematic cross-sectional view of an embodiment of a spray applicator device of the present invention.

Referring to FIG. 4, in an alternative embodiment, an optional spring 150 is positioned on distance indicator 100 between alignment member 140 that is positioned distally and spring retainer 152 positioned proximally. Spring 150 provides for a resilient positioning of the distance indicator 100 in a retrieved or proximal position, with proximal tip 120 in a proximal position. The operator deploys the indicator 100 by advancing indicator tip 110 towards tissue 90 by pushing on proximal tip 120 and compressing spring 150 until tip 110 is maximally extended. This position is shown in FIG. 4. The distance from the tissue 90 is then determined as described above, visually or tactilely, after which point the operator can adjust the distance as needed and then release proximal tip 120 which will then return distance indicator 100 to the retrieved position, i.e. most proximal position, forced by the spring 150. The operator then can initiate the spray delivery from device 20. The delivery of gas-assisted spray is performed from a distance that is equal or larger than the minimum recommended distance D.

Figure 5:
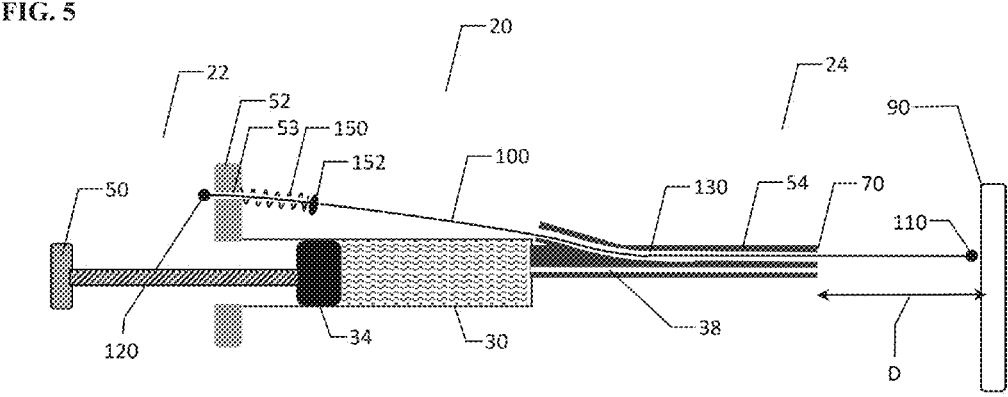
FIG. 5 shows a schematic cross-sectional view of an embodiment of a spray applicator device of the present invention.

Referring to FIG. 5, an embodiment of the present invention is shown in a side view, whereby only one of two barrels of the spray applicator device 20 is visible, specifically first barrel 30, with gas supply not shown. Indicator conduit 130 is shown entering delivery cannula 54 under angle, with wire of the distance indicator 100 passing through an alignment aperture 53 in handgrip 52. Optional spring 150 is positioned on distance indicator 100 between handgrip 52 positioned proximally and a spring retainer 152 positioned distally. Spring 150 provides for a resilient positioning of the distance indicator against tissue 90, whereby when the tip 110 is pushed against the tissue, distance indicator 100 resiliently retreats proximally, compressing the spring 150 and providing an indication to the operator that the distance is less than the minimum recommended distance D. Prior to spraying, if needed, the operator can optionally retract indicator 100 by pulling on proximal tip 120 to retrieve indicator 100 proximally and consequently to decrease any potential interference with the spray.

In an alternative embodiment (not shown) of the present invention, similarly to embodiment of FIG. 5, optional spring 150 is positioned on distance indicator 100 between handgrip 52 positioned distally and a spring retainer 152 positioned proximally and optionally unified with proximal tip 120. Spring 150 provides for a resilient positioning of the distance indicator 100 in a retrieved position, i.e. in most proximal position. The practitioner deploys the indicator 100 by advancing indicator tip 110 towards tissue 90 by pushing on proximal tip 120 and compressing spring 150 until the tip 110 is maximally extended. The distance from the tissue 90 is then determined as described above, visually or tactilely, after which point the operator can adjust the distance as needed and then release proximal tip 120 which will then return distance indicator 100 to the retrieved position, i.e. most proximal position, forced by the spring 150. The operator then can initiate the spray delivery from device 20 with no interference by the distance indicator 100 with the spray. The delivery of gas-assisted spray is performed from a distance that is equal or larger than the minimum recommended distance D.

FIGS. 1-5 illustrate the embodiments wherein cannula tip 70 does not have an atomizing spray tip, with components 32 and 42 expressed separately from conduits 38 and 48. Alternatively, spray applicator device 20 can further contain a mixer or an atomizing spray mixer, which can be positioned at the cannula tip 70, or anywhere between cannula tip 70 and exit ports 36 and 46. Gas assist can be provided into the spray mixer so that gas is intermixed with components 32 and 42 prior to exiting device 20, or gas assist can be provided in proximity to the area where pre-mixed components 32 and 42 are exiting device 20.

Figure 6:
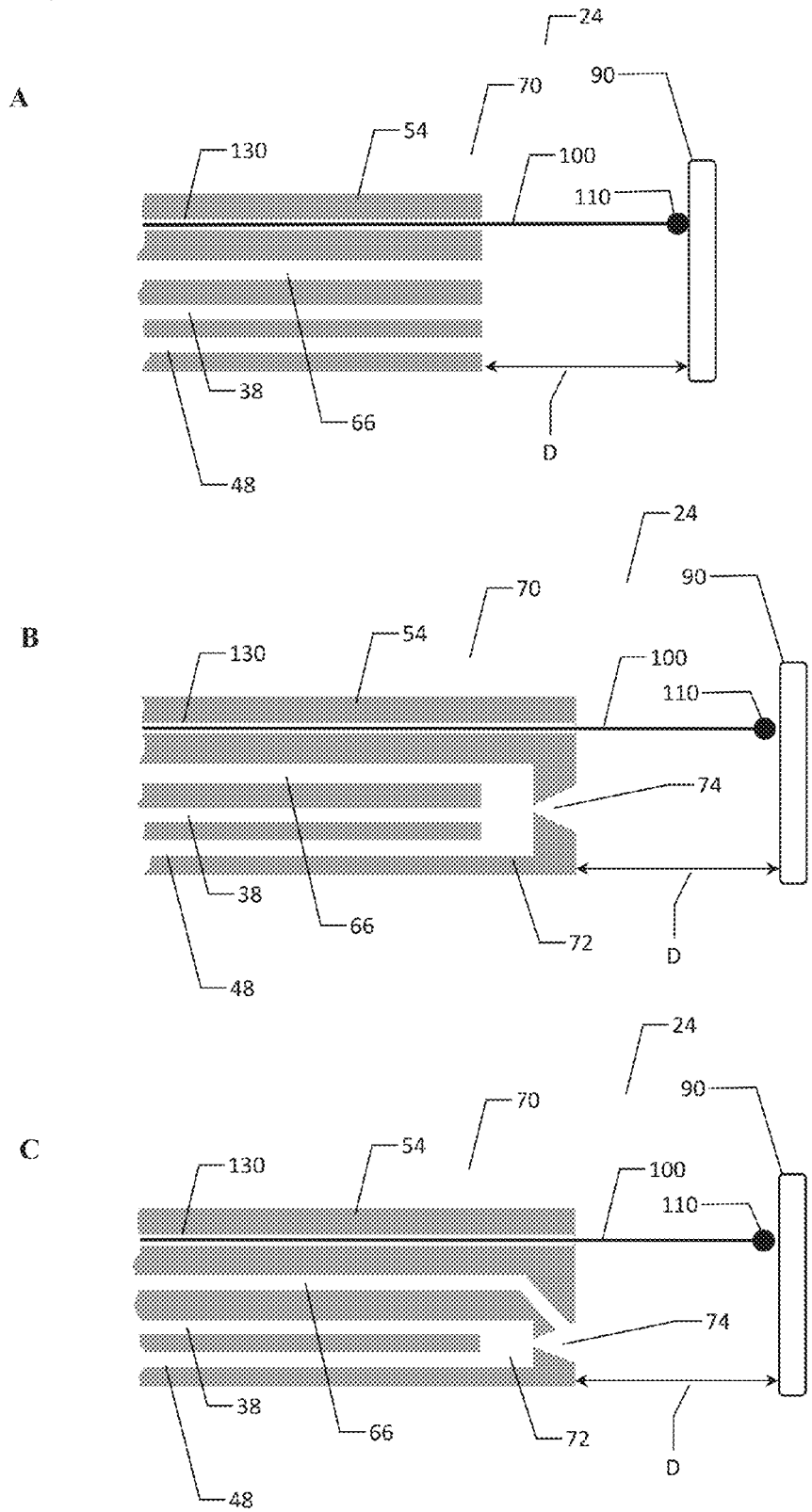
FIG. 6 shows a schematic cross-sectional view of embodiments of the cannula and the cannula tip of the present invention.

Referring now to FIG. 6, schematic cross-sectional representations of different designs of cannula 54 at the distal end 24, in the vicinity of tip 70 are shown. FIG. 6A shows delivery cannula 54 with cannula tip 70 similar to the element presented in FIGS. 1-5, showing components conduits 38 and 48, gas conduit 66, and distance indicator 100 disposed in indicator conduit 130. The medicament components are expressed separately from conduits 38 and 48 with gas discharged from gas conduit 66, all exiting in proximity to each other from tip 70 as shown.

FIG. 6B shows delivery cannula 54 with cannula tip 70 having spray mixer 72 and spray nozzle 74. Spray mixer 72 is a mixing chamber into which components are supplied via conduits 38 and 48, with gas supplied into spray mixer 72 as well via conduit 66. The mixed components are then expressed through nozzle 74 together with gas.

FIG. 6C shows delivery cannula 54 with cannula tip 70 having spray mixer 72 and spray nozzle 74. Spray mixer 72 is a mixing chamber into which components 32 and 42 are supplied via conduits 38 and 48. The mixed components are then expressed through nozzle 74, with gas supplied into nozzle 74 via conduit 66.

Other designs and arrangements of spray mixer 72 and nozzle 74 are known to these skilled in the art and can be incorporated into device 20 in combination with the distance indicator 100.

Figure 7:
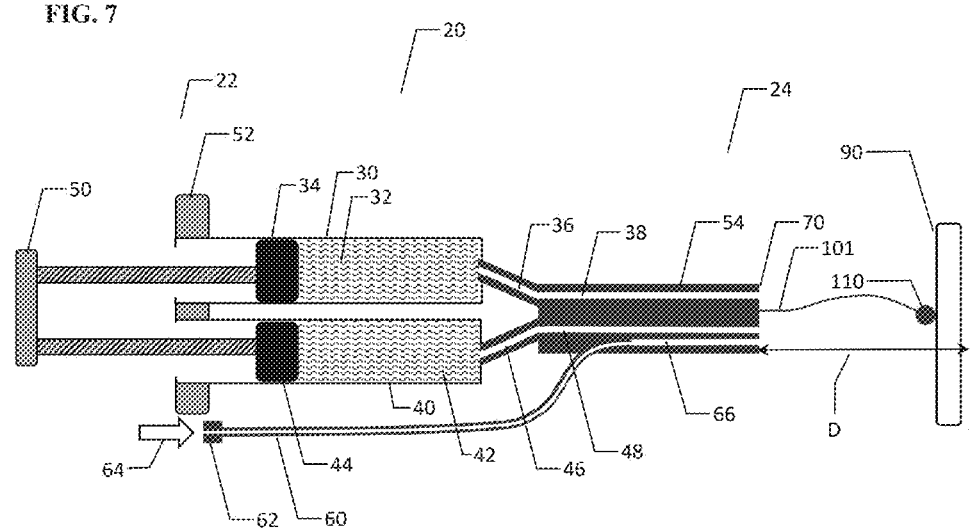
FIG. 7 shows a schematic cross-sectional view of an embodiment of a spray applicator device of the present invention.

Referring now to FIG. 7, a schematic cross-sectional representation of an alternative embodiment of the present invention is shown, whereby the fixed distance indicator 101 is not retrievable, but is affixed at the cannula tip 70. Observation or tactile feeling of bending of the fixed distance indicator 101, as shown in FIG. 7, indicates to the operator that minimum recommended distance D has been reached and cannula tip 70 is closer than the distance D. Advantageously, unlike the case of a rigid spacer, cannula tip 70 can be moved closer to tissue 90 as needed, when no gas is utilized. Device 20 ensures that spray is performed not closer than the generally or clinically recommended minimum spray distance D.

Figure 8:
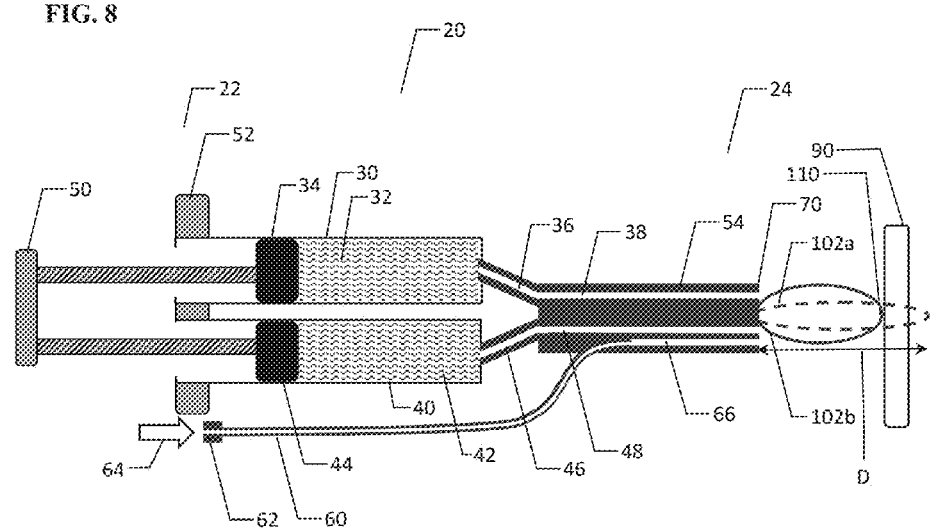
FIG. 8 shows a schematic cross-sectional view of an embodiment of a spray applicator device of the present invention.

Referring now to FIG. 8, a schematic cross-sectional representation of an embodiment of the present invention is shown, with the fixed distance indicator 102 that is not retrievable but affixed at cannula tip 70 and is in a form or shape of an elongated ellipse that is directed towards tissue 90. Ellipse 102*a* (shown in dotted line) represents the fixed distance indicator prior to contact with the tissue, and ellipse 102*b* (shown in a solid line) being in the shape of a partially collapsed ellipse is fixed distance indicator after contact with tissue, with distance to tissue 90 that is less than the generally or clinically recommended minimum distance D. The shape or form of the collapsed ellipse 102*b*, as shown in FIG. 8, indicates to the operator that minimum recommended distance D is reached and cannula tip 70 is closer than the distance D. Advantageously, unlike the case of a rigid spacer, cannula tip 70 can be moved closer to tissue 90 as needed, such as when no gas assist is utilized. Device 20 ensures that spray is performed not closer than the generally or clinically recommended minimum spray distance D.

Figure 9:
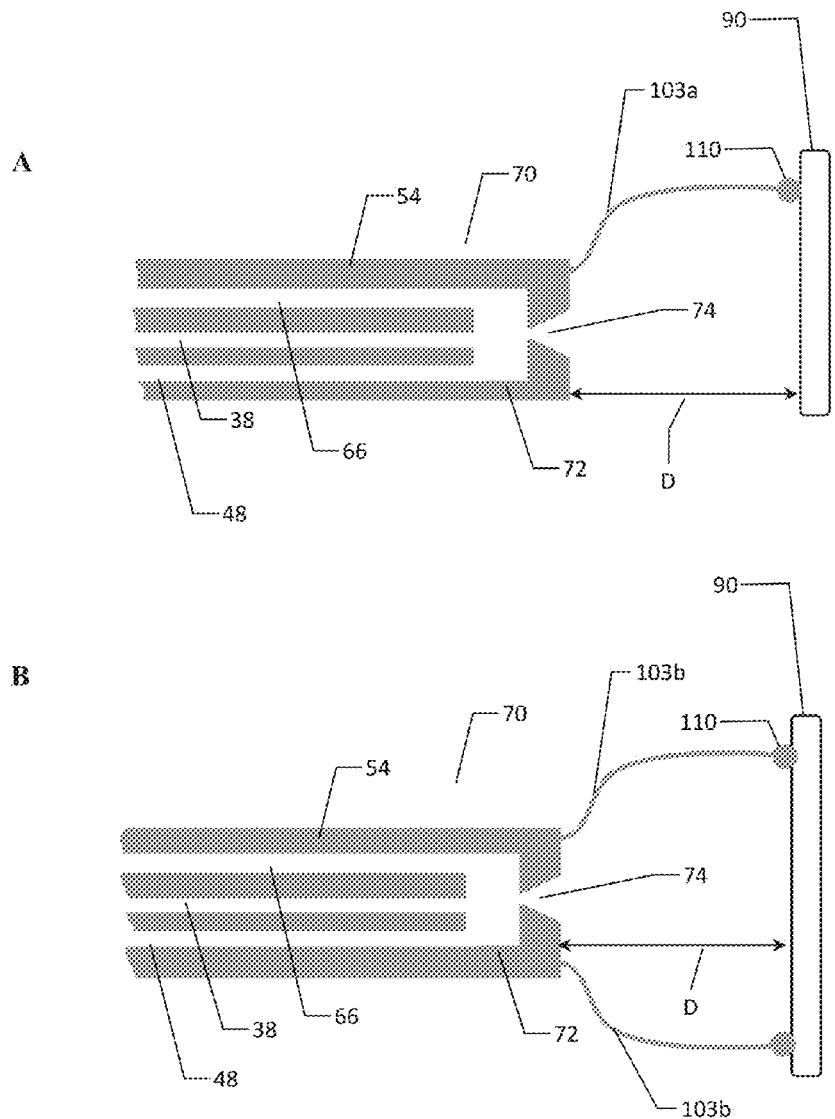
FIG. 9 shows a schematic cross-sectional view of embodiments of the cannula and the cannula tip of the present invention.

Referring now to FIG. 9, a schematic cross-sectional representation of an embodiment of the present invention is shown. The distal end of cannula 54 is shown, with cannula tip 70 shown with the one or more fixed distance indicators 103 that are not retrievable but affixed to cannula tip 70 and are provided with an angled shape 103*a* (FIG. 9A) or alternatively in a shape of a fork 103*b* (FIG. 9B), with the exposed fixed distance indicator 103 substantially out of the sealant spray. Fixed distance indicator 103 is flexible for ready insertion into a trocar and conformable for return to the initial angular or fork shape after laparoscopic deployment.

Figure 10:
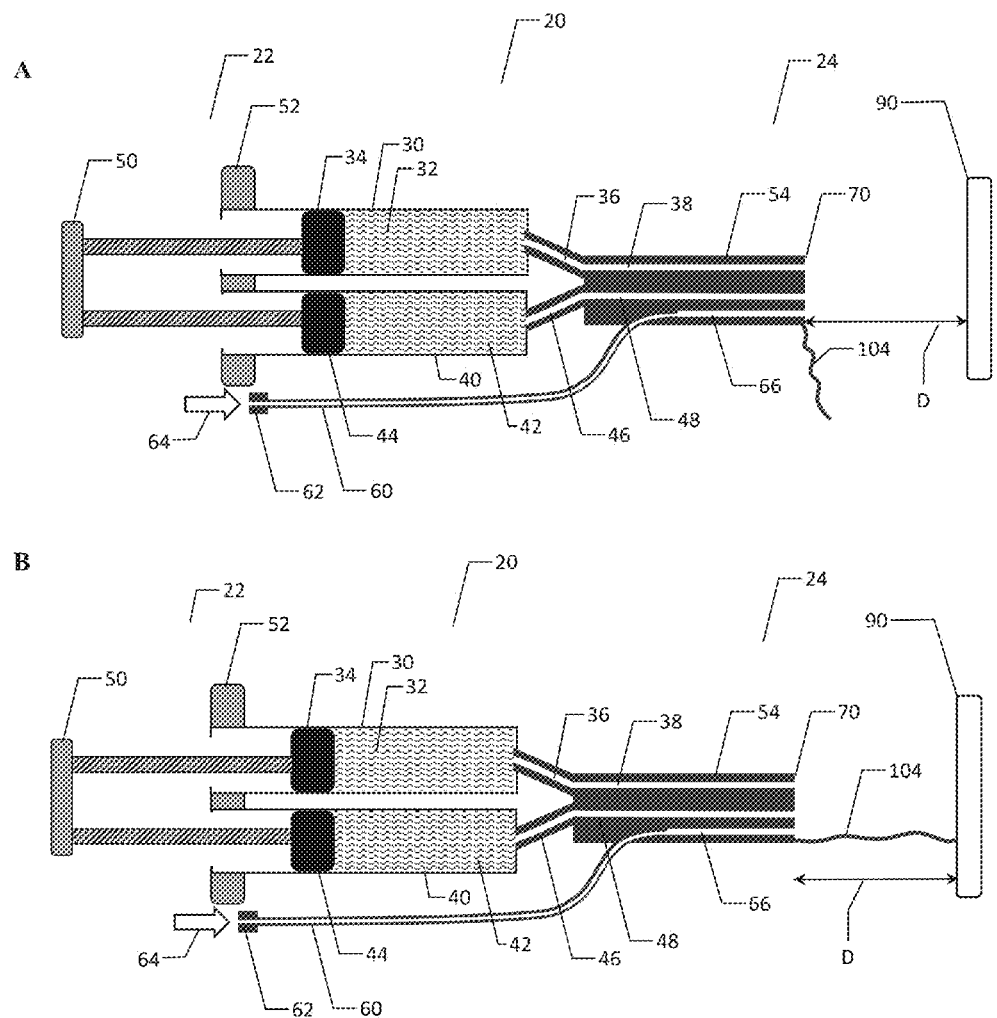
FIG. 10 shows a schematic cross-sectional view of embodiments of a spray applicator device of the present invention.

According to another aspect of the present invention, and referring now to FIG. 10, flexible string distance indicator 104 which comprises a fixed length of flexible fine string, cord, cable, line, filament, thread, or yarn, such as a fixed length of a surgical suture, is affixed to cannula tip 70 in close proximity to the exit for gas conduit 66 from delivery cannula 54. An optional knot or weight can be provided at the distal end of the string distance indicator 104 for better visibility and aerodynamics (not shown). In one aspect, with no gas assist spray, string distance indicator 104 is positioned freely outside the cannula tip 70 and projects into the gravitational field as shown in FIG. 10A. Upon activation of gas-assisted spray, string distance indicator 104 is entrained in the flow of gas and straightens in the direction of the tissue 90 to provide a direct visualization or estimate of distance D, as shown in FIG. 10B. String distance indicator 104 provides a visual means to more consistently and reliably apply the spray in accordance with the generally recognized or clinically relevant recommended guidelines.

In another aspect, the string distance indicator 104 is packed within gas conduit 66 (not shown). Upon activation of gas-assisted spray, string distance indicator 104 is expelled from gas conduit 66, entrained in the flow of gas and straightens in the direction of the tissue surface, to provide a direct visualization of the distance. Advantageously, if no gas assisted spray is used, such as in case of a drip-only spray, string distance indicator 104 does not deploy.

The length of string distance indicator 104 is about 3 cm, 4 cm, 5 cm, 8 cm, 10 cm, 12 cm, or similar lengths. The diameter of the string is form about 0.1 mm to about 1 mm, such as 0.2 mm, 0.3 mm, or 0.5 mm. The string can be a monofilament, or a braid. Optionally, string distance indicator 104 has distance indicating markings, such as colored dots or cross-lines, optionally spaced equidistantly, such as every 1 cm or every 2 cm along the string. Distances considered to be of particular importance (such as minimum recommended distances, etc.) may be indicated by additional and unique markings. In one aspect, string distance indicator 104 is adjustable so that a variable pre-selected distance from tissue 90 can be clearly indicated by the string indicator and observed by the operator.

Advantageously, string distance indicator 104 indicates distance to the tissue 90 when gas assist spray is performed under any angle, not only when the spraying is performed strictly vertically downwards i.e. from above the tissue 90 downwards vertically towards the tissue 90. The gas will entrain the string indicator and will straighten it towards the surface of tissue. The operator will be able to observe the string distance indicator 104 and the distance between the tissue 90 and the end of the string distance indicator 104, and to ensure that spraying is performed from an appropriate distance, preferably not closer than generally recognized or clinically relevant recommended minimum distance D as indicated by string distance indicator 104. Advantageously, unlike the case of a rigid spacer, cannula tip 70 can be moved closer to the tissue 90 as needed, for instance when no spray assist gas is utilized. Device 20 ensures that spray is preformed not closer than the generally recognized or clinically relevant recommended minimum spray distance D.

Referring to FIG. 11, an embodiment of the present invention is shown in a schematic cross-sectional view. Device 20 has the capability of performing gas-assisted spray, with gas supplied by connecting compressed gas source to port 62, with gas flow direction into indicator conduit 130 schematically shown by arrow 64. Gas flows through indicator conduit 130 to gas flow control chamber 160 and then into gas supply line 60 connected to gas conduit 66 within delivery cannula 54, exiting delivery cannula 54 out of the tip 70 towards tissue 90.

Distance indicator 105 is adapted to control gas delivery depending upon the distance between cannula tip 70 and tissue 90, and comprises a retractable elongated flexible wire or rod that is slidably disposed in indicator conduit 130, with length of exposed indicator 105 protruding out of cannula 54 substantially equal to D or about equal to D. Distance indicator 105 has at the distal end an indicator tip 110 that optionally comprises an enlarged indicator tip 110 which has larger dimensions relative to the diameter of distance indicator 105.

Distance indicator 105 has a gas flow control plunger 165 on the end opposite to indicator tip 110, with the gas flow control plunger 165 slidably disposed within gas flow control chamber 160 and having diameter slightly smaller than the diameter of the gas flow control chamber 160 for slidability. Gas flow control plunger 165 has a diameter larger than the diameter of the distance indicator 105 wire. Gas flow control plunger 165 can move distally and proximally within the gas flow control chamber 160 together with the movement of distance indicator 105. The most proximal position of control plunger 165, as shown in FIG. 11B, results in blockage of gas flow from gas flow control chamber 160 into gas supply line 60 and then into gas conduit 66 and prevents all or most of the gas from exiting delivery cannula 54. The distal position of control plunger 165, as shown in FIG. 11A, allows gas flow from gas flow control chamber 160 into gas supply line 60 and then into gas conduit 66 and with gas exiting delivery cannula 54. Pressurizing indicator conduit 130 and thus the gas flow control chamber 160 pushes control plunger 165 and distance indicator 105 distally, as shown in FIG. 11A.

In operation, the operator optionally inserts delivery cannula 54 through a trocar (if a procedure is being performed laparoscopically) and directs cannula tip 70 towards tissue 90. The operator then initiates gas-assisted spray towards tissue 90. When the distance between tip 70 and tissue 90 is substantially equal to or larger than the generally recognized or clinically relevant recommended minimum distance D, gas flows from compressed gas source connected to port 62 to gas flow control chamber 160 and then into gas supply line 60 and into gas conduit 66 and exits delivery cannula 54 out of the tip 70 towards tissue 90, resulting in gas-assisted spray. This scenario is illustrated in FIG. 11A.

As shown in FIG. 11B, when the distance between tip 70 and tissue 90 is less than the generally recognized or clinically relevant recommended minimum distance D, distance indicator 105 is pushed proximally by contact with tissue 90, resulting in proximal sliding of gas flow control plunger 165 in the gas flow control chamber 160, resulting in blockage of gas flow from gas flow control chamber 160 into gas supply line 60 and then into gas conduit 66 and preventing all or most of the gas from exiting delivery cannula 54. This results in spray with no gas-assist.

In this aspect of the present invention, distance indicator 105 is adapted to automatically control or fully block gas delivery depending upon distance D, with no operator input needed, and optionally to be deployed only upon initiation of gas delivery, due to advancement of the distance indicator 105 distally by gas pressure. Advantageously, blocking of gas delivery by distance indicator 105 is still allowing for non-gas assisted expression of liquid or powder tissue sealants. As shown in FIG. 11, upon the distance indicator 105 touching the tissue 90 and being pushed deeper into the device 20, the distance indicator 105 is effecting gas supply, and instantly blocking gas delivery. Advantageously, the distance indicator 105 wire (such as nitinol, a commercially available and known nickel and titanium metal alloy, or a polymer, such as polyethylene or polypropylene) is flexible and will bend freely allowing even closer approach to tissue 90, while still fully blocking gas delivery. Thus unlike the case of a rigid spacer, the spray tip can to the extent that is clinically appropriate be moved closer to tissue 90, with gas supply fully blocked to reduce the risk of embolisms. The device 20 ensures that a gas-assisted spray is performed at a distance that is not closer than the generally recognized or clinically relevant recommended minimum spray distance D.

Referring to FIG. 12, alternative embodiments of the present invention similar to embodiments of FIG. 11 are shown, but with the gas flow control chamber 160 positioned within cannula 54. Compressed gas enters indicator conduit 130 with gas flow direction schematically shown by arrow 64, then flows into gas flow control chamber 160 and then into gas conduit 66a to exit delivery cannula 54 out of tip 70 towards tissue 90.

Distance indicator 106 is adapted to control gas delivery depending upon the distance between cannula tip 70 and tissue 90, and comprises a retractable elongated flexible wire or rod, and is slidably disposed in the indicator conduit 130, with length of exposed indicator 106 protruding out of cannula 54 substantially equal to D. Distance indicator 106 has at the distal end an indicator tip 110. Distance indicator 106 has gas flow control plunger 165 on the end opposite to indicator tip 110, with the gas flow control plunger 165 slidably disposed within gas flow control chamber 160 and having diameter slightly smaller than the diameter of the gas flow control chamber 160 for slidability. Gas flow control plunger 165 has a diameter larger than the diameter of the distance indicator 106 wire. Gas flow control plunger 165 can move distally and proximally within the gas flow control chamber 160 together with movement of distance indicator 106.

The distal position of control plunger 165, as shown in FIG. 12A, results in gas flow from gas flow control chamber 160 into gas conduit 66a with gas exiting delivery cannula 54. Pressurizing the indicator conduit 130 and thus gas flow control chamber 160 optionally pushes control plunger 165 distally, resulting in position shown in FIG. 12A. An optional spring (nor shown) can be installed in gas flow control chamber 160 on distance indicator 106 to provide for default distal position of control plunger 165 and distance indicator 106 in absence of contact of indicator tip 110 with tissue 90, corresponding to position shown in FIG. 12A.

The proximal position of control plunger 165, as shown in FIG. 12B, which is a result of contact of indicator tip 110 with tissue 90 which pushes control plunger 165 and distance indicator 106 proximally, resulting in proximal sliding of gas flow control plunger 165 in the gas flow control chamber 160, results in blockage of gas flow from gas flow control chamber 160 into gas conduit 66a and prevents all or most of the gas from exiting delivery cannula 54.

Blocking of gas delivery by distance indicator 106 still allows for non-gas assist liquid sealant expression via drip spray. As shown, upon distance indicator 106 touching the tissue 90 and being pushed deeper into the device 20, distance indicator 106 automatically effects the gas supply and ultimately can block gas delivery.

Referring to FIG. 12C, an alternative embodiment of the present invention similar to embodiment of FIG. 12A is shown, but with cannula tip 70 having spray mixer 72 and spray nozzle 74. Spray mixer 72 is a mixing chamber into which components are supplied via conduits 38 and 48, with gas supplied into spray mixer 72 as well via gas conduit 66a. The mixed components are then expressed through nozzle 74.

Figure 13:
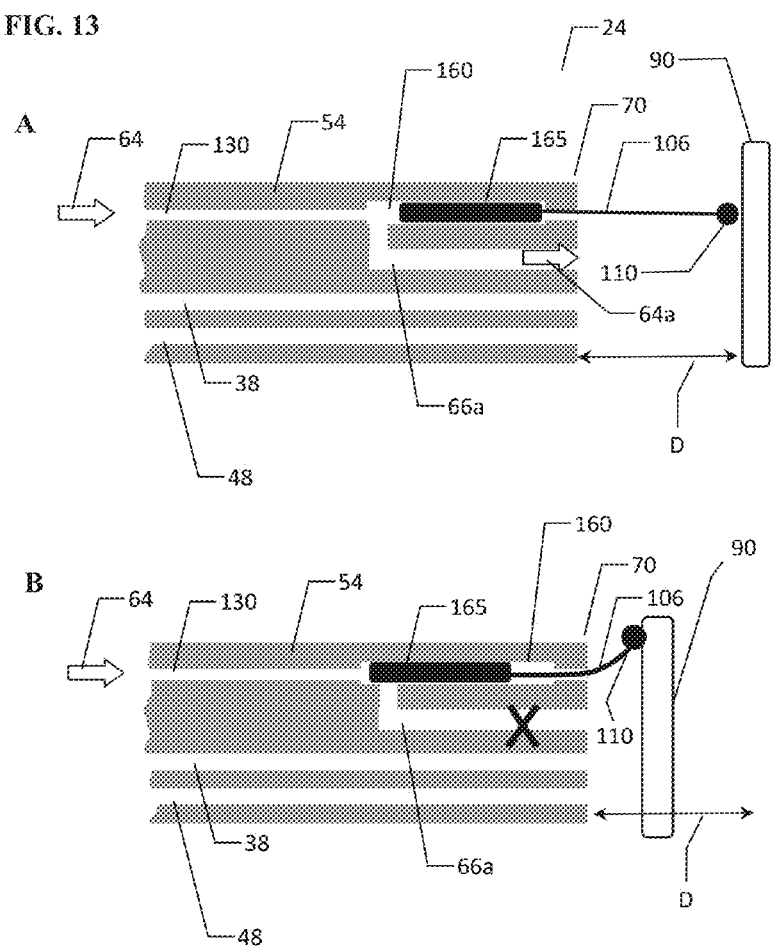
FIG. 13 shows a schematic cross-sectional view of embodiments of the cannula and the cannula tip of the present invention.

Referring to FIG. 13 embodiments of FIGS. 12A and 12B are shown in additional detail, with FIG. 13A showing gas delivery enabled with control plunger 165 positioned distally as the distance of tip 70 to tissue 90 exceeds or is equal to the generally recognized or clinically relevant recommended minimum distance D. Gas flowing out of cannula 54 is shown as arrow 64a.

FIG. 13B shows gas delivery disabled with control plunger 165 and distance indicator 106 positioned proximally with distance indicator 106 bent due to contact with tissue, as the distance to tissue 90 is less than generally recognized or clinically relevant recommended minimum distance D. This activation results in blockage of gas flow as schematically shown by sign "X" in FIG. 13B.

Figure 14:
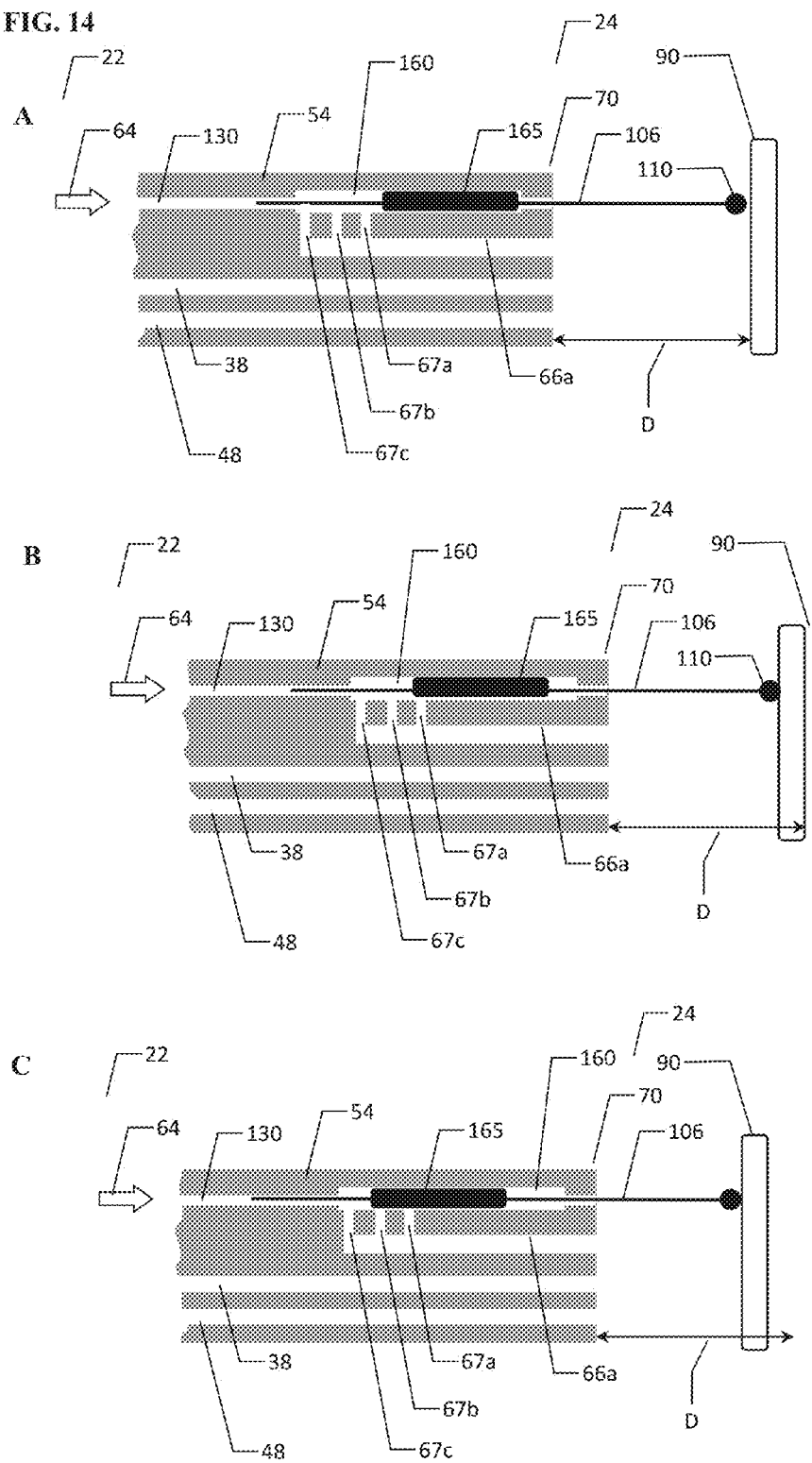
FIG. 14 shows a schematic cross-sectional view of embodiments of the cannula and the cannula tip of the present invention.

Referring to FIG. 14, in some embodiments, gas pressure can also be decreased in a variable manner whereby upon retraction of distance indicator 106 due to the contact with tissue 90, gas pressure steadily decreases due to more and more of the gas conduit(s) being blocked, until the critical distance is reached, at which point gas flow is fully blocked. FIG. 14 shows a plurality of channels 67a, 67b, 67c connecting gas flow control chamber 160 to gas conduit 66a, with channels 67a, 67b, 67c progressively blocked by gas flow control plunger 165 moving proximally within gas flow control chamber 160 upon contact with tissue 90. As tip 70 is being positioned closer and closer to tissue 90, gas flow control plunger 165 moves proximally and thus steadily decreasing gas flow out of cannula 54.

FIG. 14A shows all channels 67a, 67b and 67c fully open due to position of tip 70 farther from tissue 90 than minimum recommended distance D. FIG. 14B shows channel 67a blocked by gas flow control plunger 165 due to closer position to tissue 90 of tip 70 and proximal movement of distance indicator 106 and gas flow control plunger 165. This activation results in a decreased gas flow with gas flowing via channels 67b and 67c, which are still open.

FIG. 14C shows channels 67a and 67b blocked by gas flow control plunger 165 due to even closer position to tissue 90 of tip 70 and further proximal movement of distance indicator 106 and gas flow control plunger 165. This activation results in even more decreased gas flow, with gas flowing through the only remaining open channel 67c. Further movement of tip 70 even closer to tissue (not shown) will result in blocking of the last remaining open channel 67c and substantially stopping or minimizing any gas delivery.

In an alternative embodiment, one or more light sources, such as laser or light emitting diodes (LED) based light sources, provide at least two diverging beams that exit a light guide in proximity to the spray tip and provide light spots or images on the tissue surface. An optional focusing lens can be provided at the distal end of the light guide.

Figure 15:
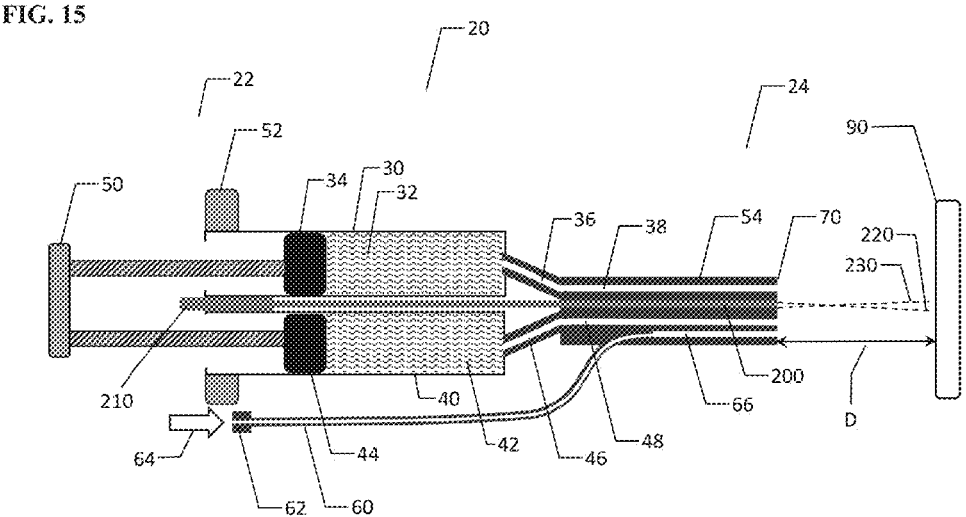
FIG. 15 shows a schematic cross-sectional view of an embodiment of a spray applicator device of the present invention.

Referring to FIG. 15, light source 210 is positioned proximally and connected to light guide 200 adapted to carry light of visible spectrum towards the distal end 24 of device 20, with light guide 200 preferably embedded into cannula 54. Light guide 200 comprises one or more fiber-optic carriers with an optional focusing lens at the distal end. There are at least two non-parallel beams of visible light 220 and 230 exiting light guide 200 towards tissue 90 as shown in FIG. 15. Light guide 200, together with light source 210, comprise yet another embodiment of the distance indicators of the present invention.

Figure 16:
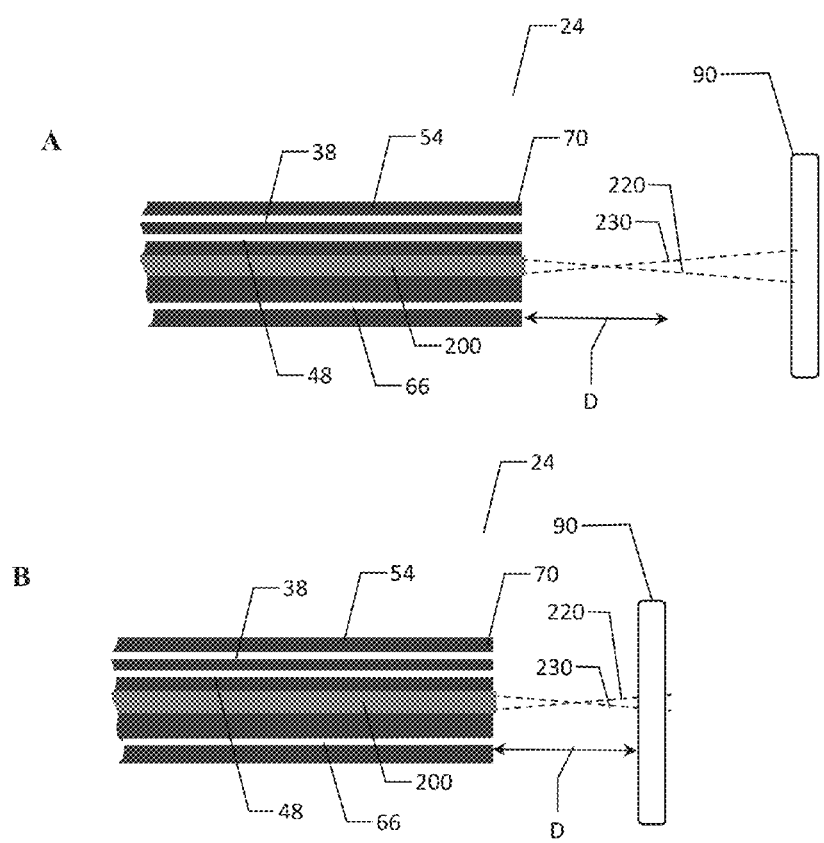
FIG. 16 shows a schematic cross-sectional view of embodiments of the cannula and the cannula tip of the present invention.

Referring to FIG. 16, the distal end of cannula 54 is shown, whereby non-parallel beams of visible light 220 and 230 exit light guide 200 towards tissue 90 and preferably cross each other at a distance about equal to the generally recognized or clinically relevant recommended minimum spray distance D, or shorter than the generally recognized or clinically relevant recommended minimum spray distance D. As can be seen in FIG. 16A, when the distance to tissue 90 is larger than D, divergence of the light spots formed on tissue by beams 220 and 230 indicates that the spray is performed at a distance that is not closer than the generally recognized or clinically relevant recommended minimum spray distance D. As shown in FIG. 16B, convergence or close proximity of the light spots formed on tissue by beams 220 and 230 indicates the spray distance is closer than the generally recognized or clinically relevant recommended minimum spray distance D and the spray tip 70 should be moved proximally i.e. further from the tissue 90.

Referring to FIG. 17, the mutual positioning of light beams spots on tissue 90 are schematically illustrated, with FIG. 17A showing the scenario corresponding to FIG. 16A, whereby divergence of the light spots 220a and 230a formed on tissue by beams 220 and 230 indicates that the spray is performed not closer than the generally recognized or clinically relevant recommended minimum spray distance D. FIG. 17B shows the scenario corresponding to FIG. 16B whereby convergence or close proximity of the light spots 220b and 230b formed on tissue by beams 220 and 230 indicates the spray distance is closer than generally recognized or clinically relevant recommended minimum spray distance D. Beams 220 and 230 can be of the same color, or they can be optionally differently colored, such as beam 220 being green and beam 230 being blue in color.

In an alternative embodiment (not shown), the non-contact sensor comprises an ultrasonic proximity sensor, having an emitter of ultrasound and a receiver of ultrasound, with both emitter and receiver optionally being the same, with the time delay between emitted ultrasonic signal and received ultrasonic signal reflected from tissue surface being used to determine the distance from tip 70 to tissue 90.

It is to be understood that the above inventive embodiments related to distance indicators apply to devices for the delivery of any medicants or therapeutic agents, including, but not limited to, two-part liquid sealants, such as systems based on fibrinogen and thrombin or thrombin analogs, forming fibrin glue upon mixing;

single component liquid sealants, such as synthetic sealants powdered medicants, such as gelatin, collagen, fibrinogen, thrombin, oxidized regenerated cellulose, and combinations thereof; and co-spray of liquid medicant and powdered medicants.

The above embodiments related to distance indicators are preferably used in cases of gas assisted delivery or when gas assisted delivery can be used as an option. However, in alternative embodiments, the inventive distance indicators can be utilized for non-gas-assisted delivery to tissue from optimal distance or at safe distances equal to or exceeding the recommended or optimal distance.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

What is claimed is:

1. A spray applicator for delivery of a medicant onto a tissue surface comprising
   a) a container containing a medicant and positioned at a proximal end of the spray applicator;
   b) a spray tip positioned at a distal end of the spray applicator;
   c) a cannula connecting the container with the spray tip;
   d) a dispensing mechanism at the proximal end of the applicator to express the medicant from the container through the cannula and the spray tip toward the tissue surface;
   e) a distance indicator that is deployable between the spray tip and the tissue surface and provides visual or tactile observation indicia of a distance between the spray tip and the tissue surface but does not prevent positioning of the spray tip closer to the tissue than the observed distance; and
   f) an optional pressurized gas source in fluid communication with the spray tip through the cannula providing gas in the vicinity of the spray tip or within the spray tip,
   wherein said distance indicator is a flexible wire, rod, string, cord, cable, line, filament or thread, all having a defined length,
   wherein said distance indicator moderates or fully blocks gas delivery to the spray tip when the distance indicator touches the tissue surface.

2. The spray applicator of claim 1 wherein said container is integral with the spray applicator and said spray tip is laparoscopically deployable.

3. The spray applicator of claim 1 wherein the medicant is selected from the group consisting of a liquid tissue sealant, at least one liquid hemostatic agent, at least one powdered hemostatic agent and combinations thereof.

4. The spray applicator of claim 1 wherein said medicant is a fibrin glue composition comprising fibrinogen and thrombin.

5. The spray applicator of claim 1 wherein said distance indicator has at least one observable distance indicating marking.

6. The spray applicator of claim 1 wherein said distance indicator is deployable and/or retrievable from the proximal end of the spray applicator.

7. The spray applicator of claim 1 wherein said distance indicator is an elongated flexible wire deployable from the cannula and optionally retrievable into the cannula, wherein a distal portion of said distance indicator extends directionally towards the tissue and said distal portion has a length equal to the defined length.

8. A method for spraying the medicant onto the tissue surface comprising operating the spray applicator of claim 1 to deploy the distance indicator towards the tissue surface.

9. The method according to claim 8 further comprising the steps of observing the distance indicator and, if necessary, adjusting the distance between the spray tip and the tissue surface to be greater than a minimum generally recognized or clinically relevant recommended spray distance and then expressing medicant onto the tissue surface via a gas-assisted spray.

10. A spray applicator for delivery of a medicant onto a tissue surface comprising
   a) a container containing a medicant and positioned at a proximal end of the spray applicator;
   b) a spray tip positioned at a distal end of the spray applicator;
   c) a cannula connecting the container with the spray tip;
   d) a dispensing mechanism at the proximal end of the applicator to express the medicant from the container through the cannula and the spray tip toward the tissue surface;
   e) a distance indicator that is deployable between the spray tip and the tissue surface and provides visual or tactile observation indicia of a distance between the spray tip and the tissue surface but does not prevent positioning of the spray tip closer to the tissue than the observed distance; and
   f) an optional pressurized gas source in fluid communication with the spray tip through the cannula providing gas in the vicinity of the spray tip or within the spray tip, wherein said distance indicator is a flexible wire, rod, string, cord, cable, line, filament or thread, all having a defined length, wherein said distance indicator comprises a flexible material of appropriate size and length to be entrained in a discharging gas delivered through the cannula in the vicinity of the spray tip.

11. The spray applicator of claim 10 wherein said container is integral with the spray applicator and said spray tip is laparoscopically deployable.

12. The spray applicator of claim 10 wherein the medicant is selected from the group consisting of a liquid tissue sealant, at least one liquid hemostatic agent, at least one powdered hemostatic agent and combinations thereof.

13. The spray applicator of claim 10 wherein said medicant is a fibrin glue composition comprising fibrinogen and thrombin.

14. The spray applicator of claim 10 wherein said distance indicator has at least one observable distance indicating marking.

15. The spray applicator of claim 10 wherein said distance indicator is deployable and/or retrievable from the proximal end of the spray applicator.

16. The spray applicator of claim 10 wherein said distance indicator is an elongated flexible string deployable from the cannula and optionally retrievable into the cannula, wherein a distal portion of said distance indicator has a length equal to the defined length.

17. A method for spraying the medicant onto the tissue surface comprising operating the spray applicator of claim 10 to deploy the distance indicator towards the tissue surface.

18. The method according to claim 17 further comprising the steps of observing the distance indicator and, if necessary, adjusting the distance between the spray tip and the tissue surface to be greater than a minimum generally recognized or clinically relevant recommended spray distance and then expressing medicant onto the tissue surface via a gas-assisted spray.

* * * * *